US008225641B2

(12) United States Patent
Wang et al.

(10) Patent No.: US 8,225,641 B2
(45) Date of Patent: Jul. 24, 2012

(54) NANOFIBERS AND METHODS OF MAKING SAME AND USING SAME IN HUMIDITY SENSORS

(75) Inventors: Ce Wang, Changchun (CN); Hongnan Zhang, Changchun (CN); Zhenyu Li, Changchun (CN); Wei Zheng, Changchun (CN); Wei Wang, Changchun (CN); Changkun Liu, Lawrenceville, NJ (US); Bing Zhou, Cranbury, NJ (US)

(73) Assignee: Headwaters Technology Innovation, LLC, Lawrenceville, NJ (US)

( * ) Notice: Subject to any disclaimer, the term of this patent is extended or adjusted under 35 U.S.C. 154(b) by 350 days.

(21) Appl. No.: 12/544,989

(22) Filed: Aug. 20, 2009

(65) Prior Publication Data
US 2010/0043529 A1 Feb. 25, 2010

Related U.S. Application Data

(60) Provisional application No. 61/090,516, filed on Aug. 20, 2008, provisional application No. 61/090,511, filed on Aug. 20, 2008.

(51) Int. Cl.
*G01N 19/10* (2006.01)
(52) U.S. Cl. .................. 73/29.02; 73/29.05; 264/172.11; 977/840; 977/902
(58) Field of Classification Search .................. 73/29.02, 73/29.05; 264/172.11; 977/840, 902
See application file for complete search history.

(56) References Cited

U.S. PATENT DOCUMENTS

| 6,653,022 | B2 * | 11/2003 | Nordlinder et al. ........... 429/232 |
| 6,679,250 | B2 | 1/2004 | Walker et al. |
| 7,013,708 | B1 * | 3/2006 | Cho et al. ..................... 73/31.05 |
| 7,264,762 | B2 | 9/2007 | Ko et al. |
| 7,354,546 | B2 | 4/2008 | Kim et al. |
| 7,393,699 | B2 | 7/2008 | Tran |
| 2003/0215624 | A1 | 11/2003 | Layman et al. |
| 2005/0069457 | A1 | 3/2005 | Huang et al. |
| 2005/0081625 | A1 * | 4/2005 | Chen et al. ................. 73/335.02 |
| 2006/0078468 | A1 | 4/2006 | Gabriel et al. |
| 2006/0226580 | A1 | 10/2006 | Xia et al. |
| 2006/0257339 | A1 * | 11/2006 | Quadir ............................ 424/61 |
| 2007/0009736 | A1 * | 1/2007 | Chuang et al. ................ 428/364 |
| 2007/0086921 | A1 | 4/2007 | Visel et al. |

(Continued)

FOREIGN PATENT DOCUMENTS
CN 1873064 12/2006
(Continued)

OTHER PUBLICATIONS

Ou, H.H. et al., Review of Titania Nanotubes Synthesized via the Hydrothermal Treatment: Fabrication, Modification, and Application, Separation and Purification Technology, vol. 58, 2007, pp. 179-191.*

(Continued)

*Primary Examiner* — Daniel Larkin
(74) *Attorney, Agent, or Firm* — Workman Nydegger

(57) ABSTRACT

A self-cleaning humidity sensor based on $Mg^{2+}/Na^+$-doped $TiO_2$ nanofiber mats is provided. Examples show the response and recovery characteristic curves for ten circles with the RH changing from 11% to 95%. The nanofibers are manufactured by mixing together a metal salt comprising titanium, a magnesium compound, a sodium compound, and a high molecular weight material to form a mixture, electrospinning the mixture to form composite nanofibers, and calcining the composite nanofibers to yield a $TiO_2$ nanofiber material doped with magnesium and sodium.

20 Claims, 10 Drawing Sheets

U.S. PATENT DOCUMENTS

2007/0116640 A1 5/2007 Kim et al.
2010/0005858 A1* 1/2010 Virji et al. .................... 73/31.05

FOREIGN PATENT DOCUMENTS

JP 2007-009398 1/2007
KR 2004/0078921 9/2004
TW 244231 11/2005

OTHER PUBLICATIONS

Sen'i Gakkaishi, "Establishment of Nanofiber Preparation Technique by Electrospinning", vol. 64, No. 1, pp. 24 (2008), Abstract.

* cited by examiner

னாNOFIBERS AND METHODS OF MAKING SAME AND USING SAME IN HUMIDITY SENSORS

RELATED APPLICATIONS

This application claims the benefit of earlier filed U.S. Provisional Application No. 61/090,516, filed Aug. 20, 2008, and also U.S. Provisional Application No. 61/090,511, filed Aug. 20, 2008, the disclosures of which are incorporated herein in their entirety.

BACKGROUND OF THE INVENTION

1. Field of the Invention

The invention is in the field of humidity sensors, more particularly humidity sensors that include nanofibers on an electrode for use in measuring the relative humidity of a gaseous mixture.

2. Technology Review

One-dimensional (1D) nanostructures such as wires, rods, tubes, and fibers have attracted intensive research driven by their unique applications in mesoscopic physics and fabrication of nanodevices. Until now, many types of functional devices based on 1D functional material have been successfully fabricated, including optoelectronic devices, gas/humidity sensors, photochromic devices, and supercapacitors. Among these functional devices, humidity sensors have gained special focus owing to their practical applications in air-quality control, environmental monitoring, healthcare, defense and security, etc. Since the humidity-sensitive electrical conduction has been established by Jain and his coworkers, many efforts have been focused on the synthesis of humidity sensors with perfect characteristics. With the need for high sensitive and stable humidity sensors, many efficient humidity sensors have been fabricated based on 1D metallic oxide nanostructures taking the advantages of thermal, physical and chemical stability and their porous nature.

BRIEF SUMMARY OF THE INVENTION

This invention relates to a method of fabricating a humidity nanosensor using an electrical spinning method. The humidity nanosensors manufactured according to the invention include nanofibers supported on an electrode. The nanofibers can be in the form of a mat and can include $TiO_2$ nanofibers doped with magnesium and sodium. The doped nanofibers have been found to be substantially more sensitive to humidity than $TiO_2$ sensors manufactured using other techniques and compositions.

In one embodiment, a method includes: 1) mixing together a titanium compound, a magnesium compound, a sodium compound, and a high molecular weight material; 2) electrospinning the mixture to form composite nanofibers; and 3) calcining the composite nanofibers to yield a $TiO_2$ nanofiber material doped with magnesium and sodium. The high molecular weight material used to manufacture the composite nanofibers can be a polymer such as, but not limited to, polyvinyl alcohol and/or polyvinyl pyrrolidone (Mw greater than about 250,000, preferably greater than about 500,000, more preferably greater than about 1,000,000. In one embodiment, the composite nanofiber can be calcined at a temperature in a range from 500° C. and 650° C., and preferably above about 600° C.

The nanofibers manufactured according to the invention can be deposited on an electrode to form a nanosensor. In one embodiment, the electrode is an interdigital electrode, and the nanofibers are deposited on the electrode as a mat of fibers.

The nanofibers can have a width in a range of about 10 nm to about 600 nm, preferably a width in a range of about 50 nm to about 300 nm.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which.

DETAILED DESCRIPTION

Embodiments of this the present invention provide a method of fabricating ceramic nanometer fibers for humidity detection using an electrical spinning method.

I. Fabrication of Mg2+ and Na+-Doped $TiO_2$ Nanofiber Mats

Figure 1:
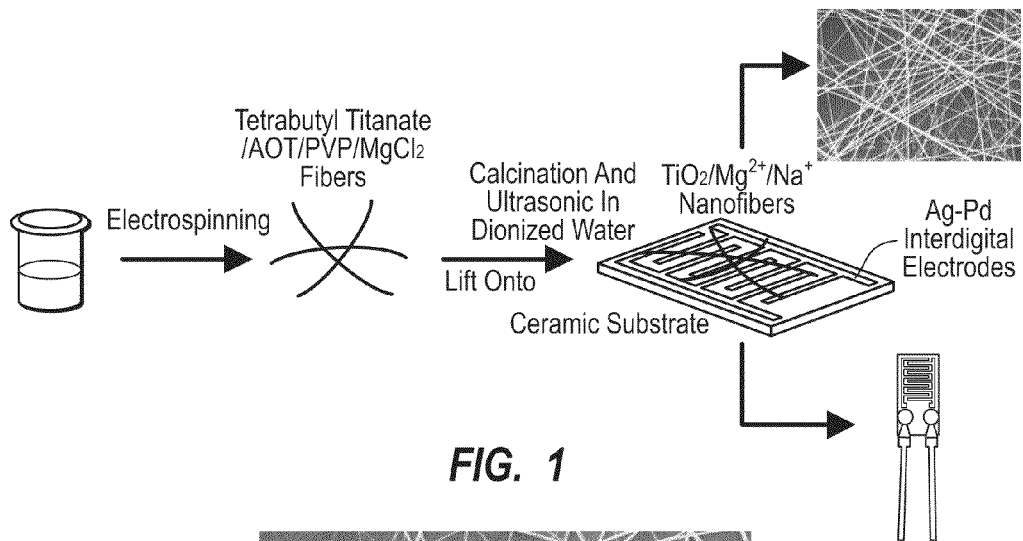
FIG. 1 is a schematic diagram of the steps to fabricate $Mg^{2+}/Na^{+}$-doped $TiO_2$ nanofiber mats for humidity measurement via electrospinning and calcination.

Electrospinning is used to fabricate $MgCl_2$/dioctyl sulfosuccinate sodium (AOT: $C_{20}H_{37}OSNa$)/poly (vinyl pyrrolidone) (PVP)/tetrabutyl titanate nanocomposite fibers. Thereafter, calcination at 500° C. in air for 3 hours is used to treat the as-prepared nanocomposite fibers to remove PVP and convert tetrabutyl titanate into crystal $TiO_2$ nanofibers. Finally, $Mg^{2+}$- and $Na^+$-doped $TiO_2$ nanofiber mats are ultrasonicated in deionized water for 5 minutes and lifted onto the working electrode for sensor measurement. To see the whole procedure clearly, all the steps have been schematically illustrated in FIG. 1. As illustrated in FIG. 1, the compositions in the final product can be easily controlled by varying the compositions in precursors.

II. Morphological and Structural Characterization

Figure 2A:
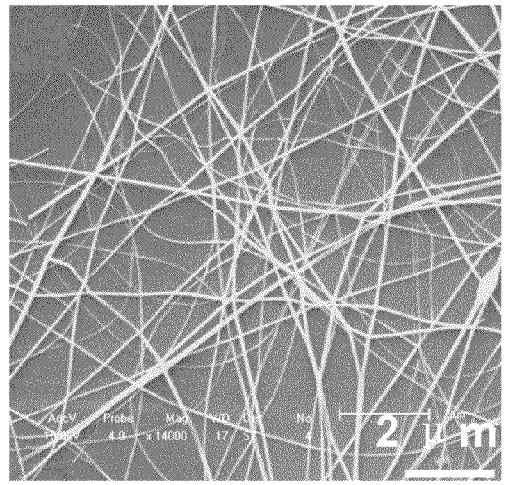
FIGS. 2a-d are SEM images of the as-prepared products; the contents of $MgCl_2$ in the products are a) 14.3%, b) 22.2%, and c) 40.0%, respectively; d) shows XRD patterns of the pure $TiO_2$ nanofiber mats and hybrids systems.
Figure 2B:
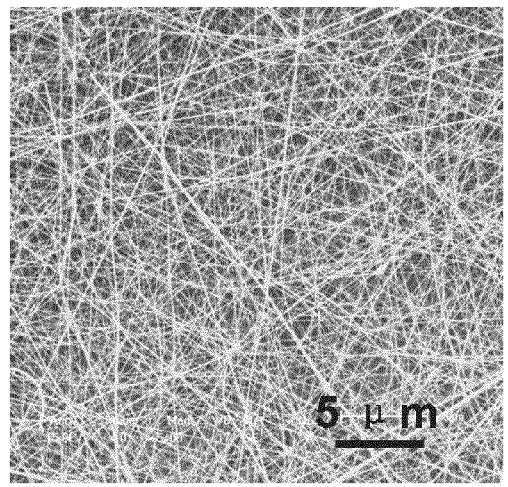
Figure 2C:
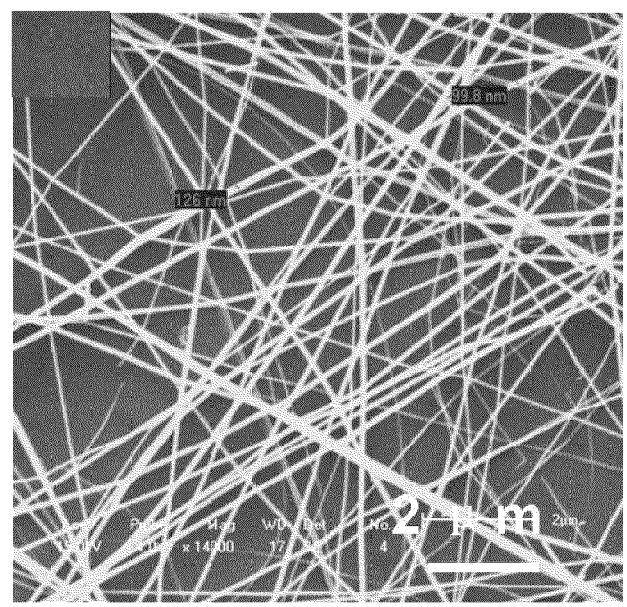

FIGS. 2a-c are SEM images of the products containing different contents of $MgCl_2$ in the final products by keeping the amount of AOT at 0.02 g, indicating the large scale of the products with the diameters ranging from 50 to 300 nm can be obtained. Increasing the contents of $MgCl_2$ in the products from 14.3%, to 22.2%, and to 40.0%, the diameters of the products become thinner for more charges have been added during the process of electrospinning. FIG. 1d shows the XRD of the products. Comparing with the pure $TiO_2$ nanofiber mats (polycrystals containing rutile and anatase), Those $TiO_2$ nanofibers in the hybrids systems are anatase, implying that the addition of $Mg^{2+}/Na^+$ can change the microstructures of the $TiO_2$ nanofibers during the calcination.

III. Humidity Sensitive Properties

Figure 3A:
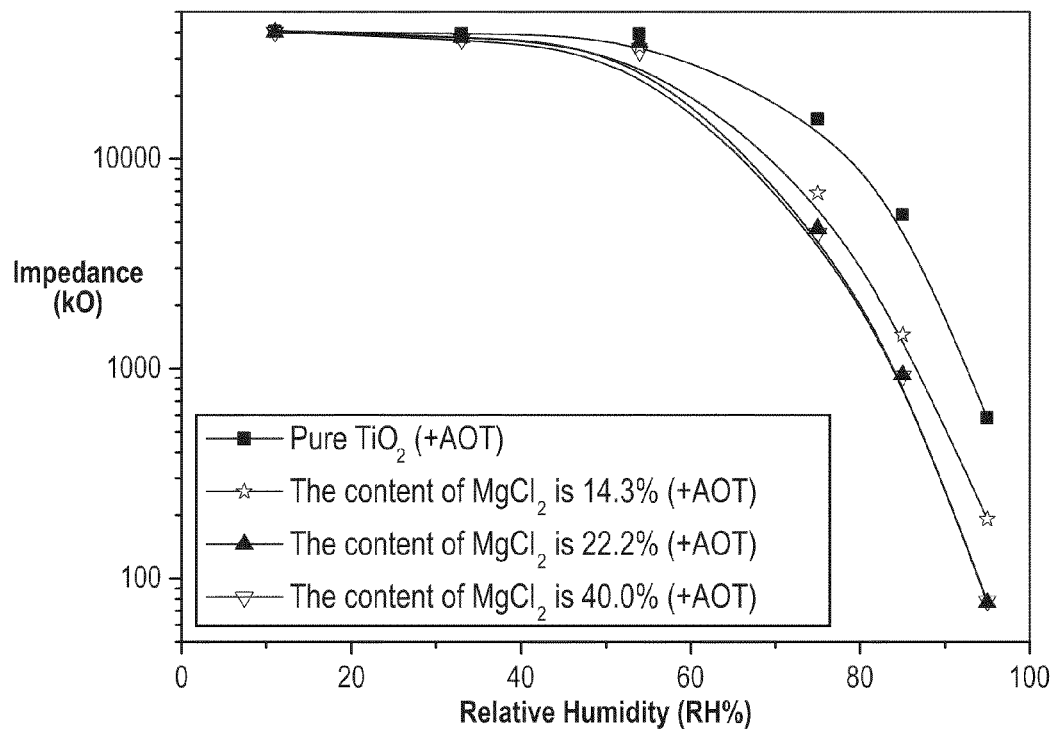
FIGS. 3a-b are graphs that depict a) dependence of impedance on the relative humidity for the products and b) humidity hysteresis characteristic of the products containing 22.2% $MgCl_2$.

A. 2.3.1. Impedance—Relative Humidity (RH) Curves and Humidity Hysteresis Characteristic During the process of humidity measurement, the operation AC voltage and frequency are kept at 1 V and 100 Hz (see Supporting Information below), respectively. FIG. 3a is a graph that shows the dependence of impedance on the relative humidity (RH) for $TiO_2$ nanofibers containing different contents of $Mg^{2+}/Na^+$. In contrast to the pure $TiO_2$ nanofiber mat, $Mg^{2+}/Na^+$ doped $TiO_2$ nanofiber mats show better sensitivity. The $TiO_2$ nanofiber mat with the content of $MgCl_2$ at 22.2% shows the best linearity. From FIG. 3a, it can also be observed that when the relative humidity ranged from 11% to 54%, the impedance of the product did not vary much. This phenomenon might be interpreted in the way that, when $MgCl_2$ in the final products is incorporated in the $TiO_2$ matrices, it is difficult to dissolve into $Mg^{2+}$ and $Cl^-$, as the RH is low. From the above results, the content of $MgCl_2$ is kept in the following experiment.

Figure 3B:
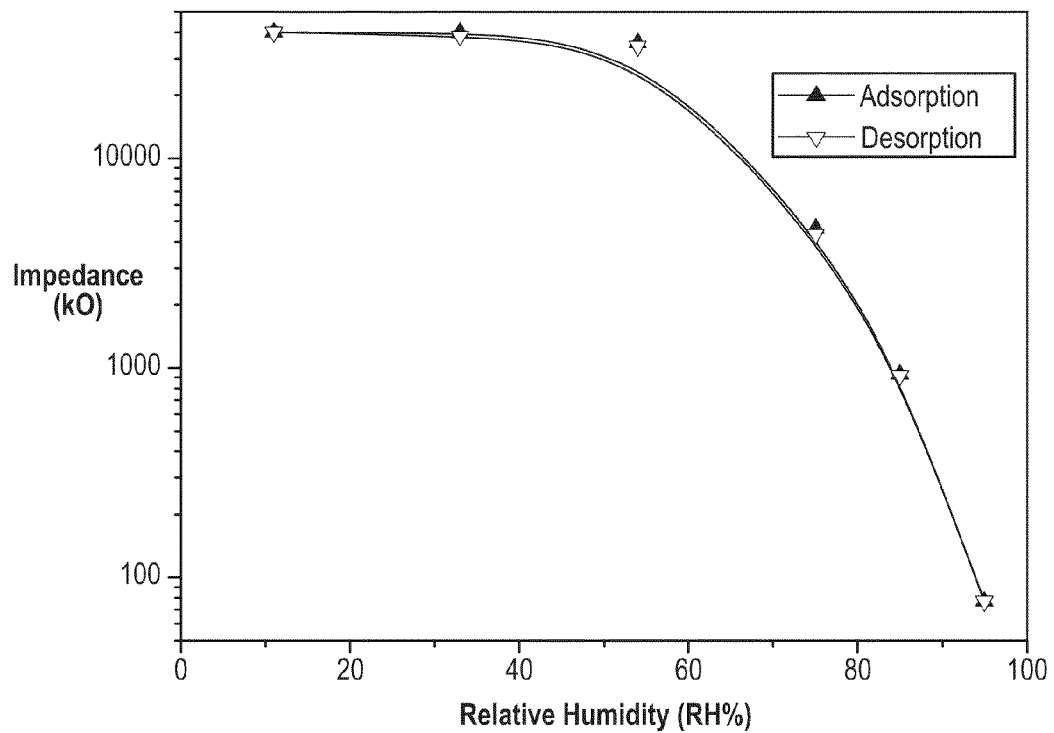

FIG. 3b is a graph that shows the humidity hysteresis characteristic of the as-prepared product. Two lines, representing adsorption and desorption process respectively, are perfectly inosculated, which surpassed all the results reported before.

B. Response and Recovery Behavior

Figure 4A:
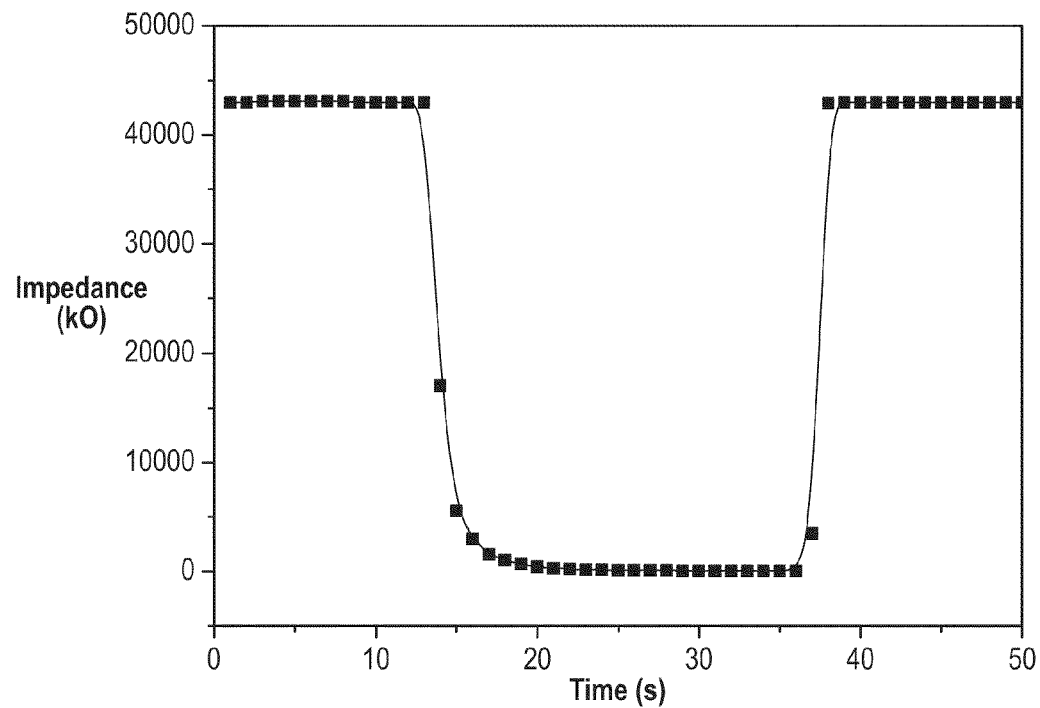
FIGS. 4a-b are graphs that depict a) response and recovery characteristic curves for one cycle and b) ten cycles with the relative humidity ranging from 11 to 95%; the content of $MgCl_2$ in the product is 22.2%.
Figure 4B:
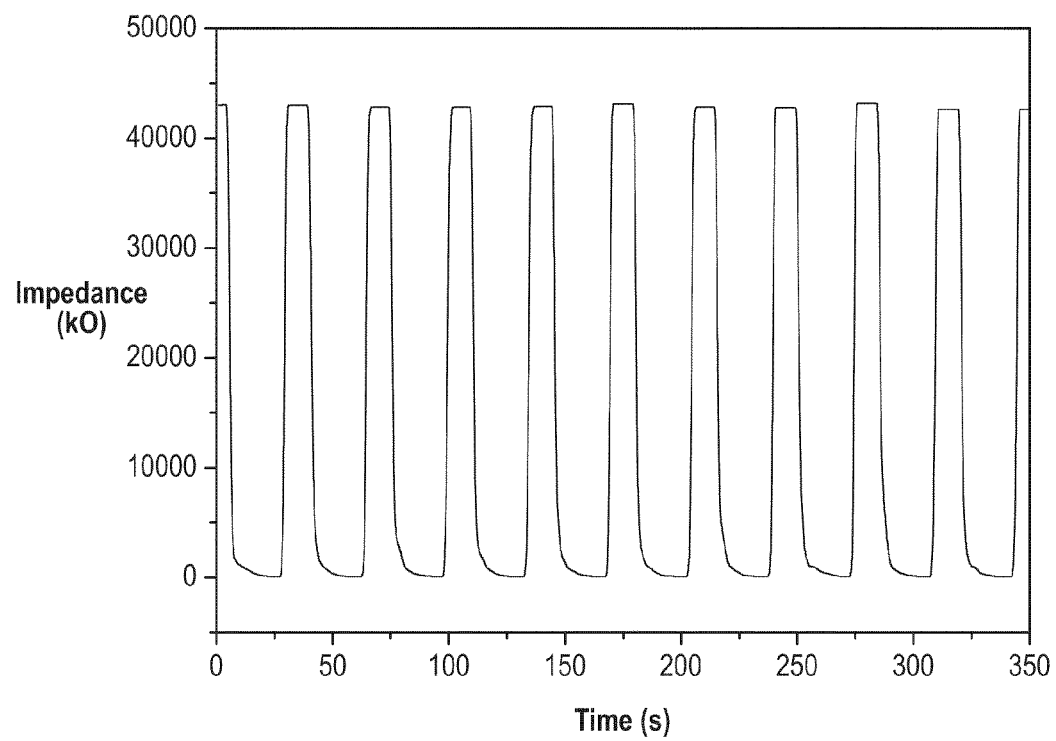

FIGS. 4a-b indicate the response and recovery behaviors, an important humidity characteristic, have been measured on the inventive products. FIG. 4a is a graph that shows the response and recovery characteristic curves for one cycle with the relative humidity changing from 11% to 95%. When the relative humidity increases from 11% to 95%, the response time is about 3 sec. As the relative humidity lowers from 95% to 11%, the recovery time is about 2 seconds.

FIG. 4b is a graph that shows the response and recovery curves for ten cycles, revealing that the highest and lowest impedance of the as-prepared product is relatively stable, confining the good stability. The response and recovery behaviors of the product might be caused by the structures of 1D $TiO_2$ nanofibers (substrates). The large surface of substrate facilitates absorption of the water molecules on the outer surface of the products so that $MgCl_2$ dissolves into $Mg^{2+}$ and $Cl^-$ and changes the impedance. Moreover, the 1D substrate facilitates fast mass transfer of the water molecules to form an interaction region and cause the charge carriers to transverse the barriers induced by molecular recognition along the substrate. The humidity sensing working principles have been discussed in the Supporting Information below.

IV. Affection of $TiO_2$ Nanofibers' Structurs on Humidity Characteristic

Figure 5A:
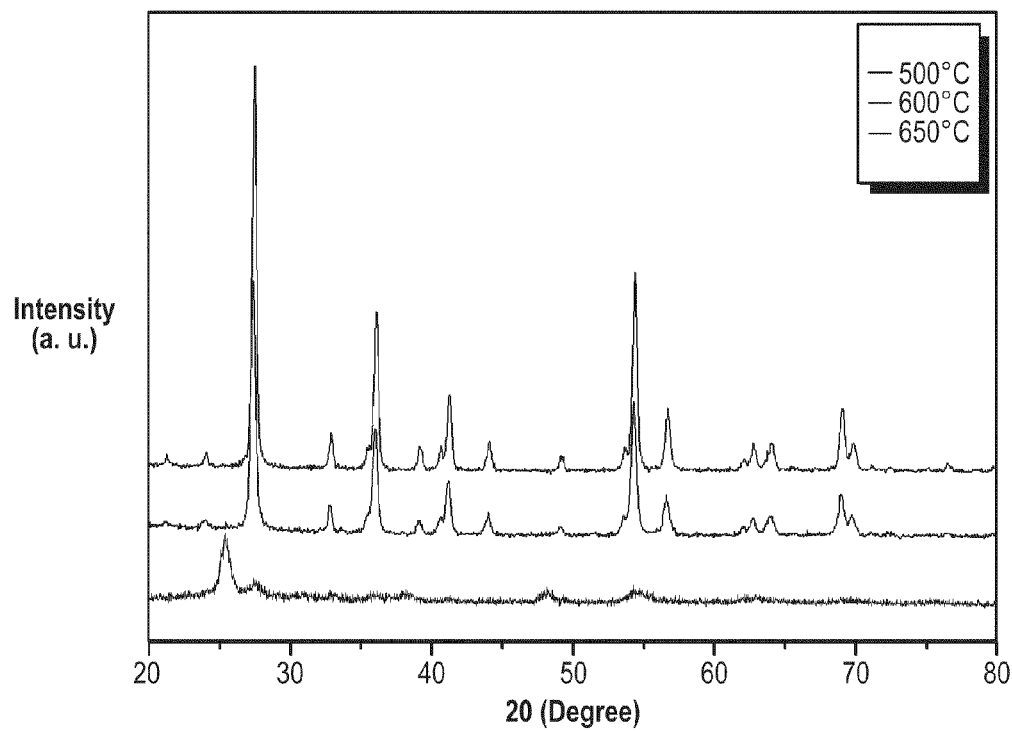
FIGS. 5a-f are graphs that depict a) XRD patterns, b) dependence of impedance on the RH, c) response and recovery behaviors for the products calcinated at different temperatures, d) humidity hysteresis of the product annealed at 650° C., and e) and f) are response and recovery behaviors of the product annealed at 650° C. for one circle and ten circles, respectively; the content of $MgCl_2$ in the product is 22.2%.

The crystal structures of $TiO_2$ substrates are changed by altering the calcinating temperatures in order to observe their effects on humidity characteristics. FIG. 5a shows the XRD of the products by increasing the annealing temperatures from 500° C. to 600° C., and to 650° C. From the XRD patterns, it can be seen that those $TiO_2$ structures are rutile crystals when the temperatures are above 600° C.

Figure 5B:
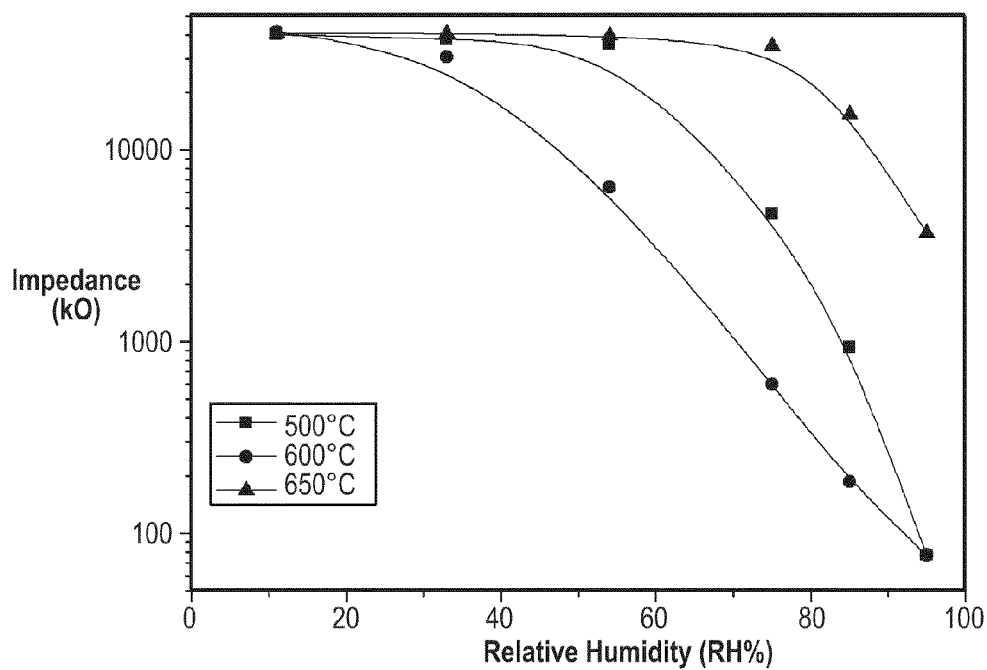

FIG. 5b shows the dependence of impedance on the relative humidity (RH) for $TiO_2$ nanofibers with different crystal structures, indicating those $Mg^{2+}/Na^+$ doped $TiO_2$ nanofibers, calcinated at 600° C., has the best linearity owing to the rutile $TiO_2$ (110), which plays as active sites for water dissociation, making the impedance of the product change. When the temperature was 650° C., the linearity was destroyed in this particular example. This phenomenon could be explained in the way that when the temperature is too high, $Mg^{2+}$ will react with $TiO_2$ and $MgTiO_3$ will be formed, which is difficult to dissolve into $Mg^{2+}$ and $TiO_3^{2-}$, making impedance unchanged.

Figure 5C:
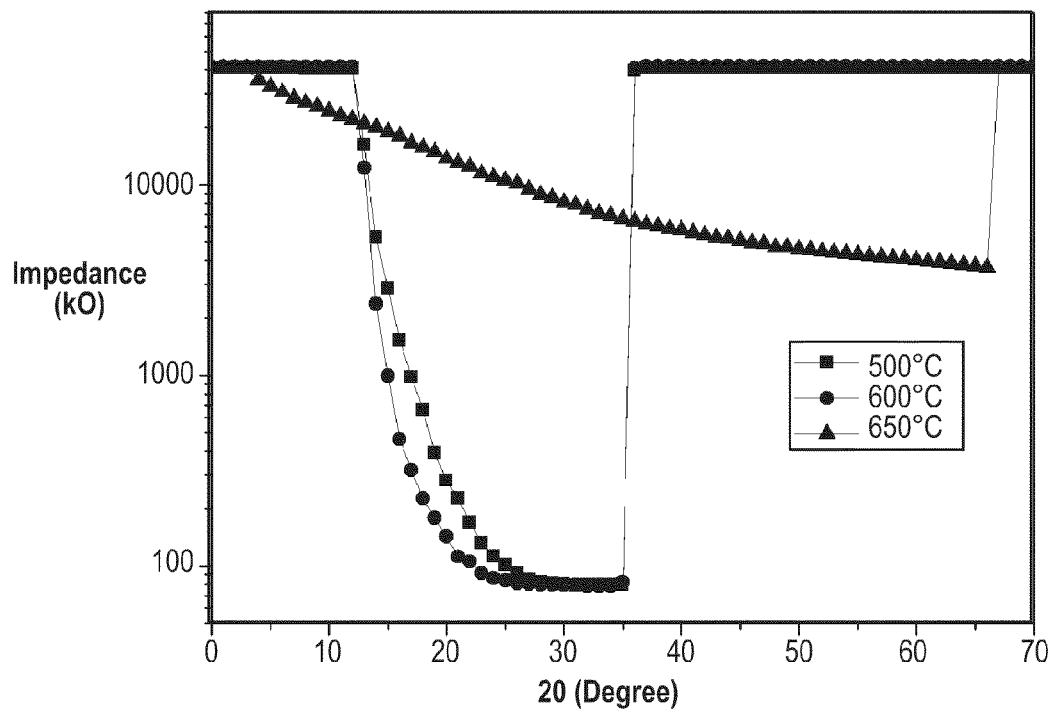
Figure 5D:
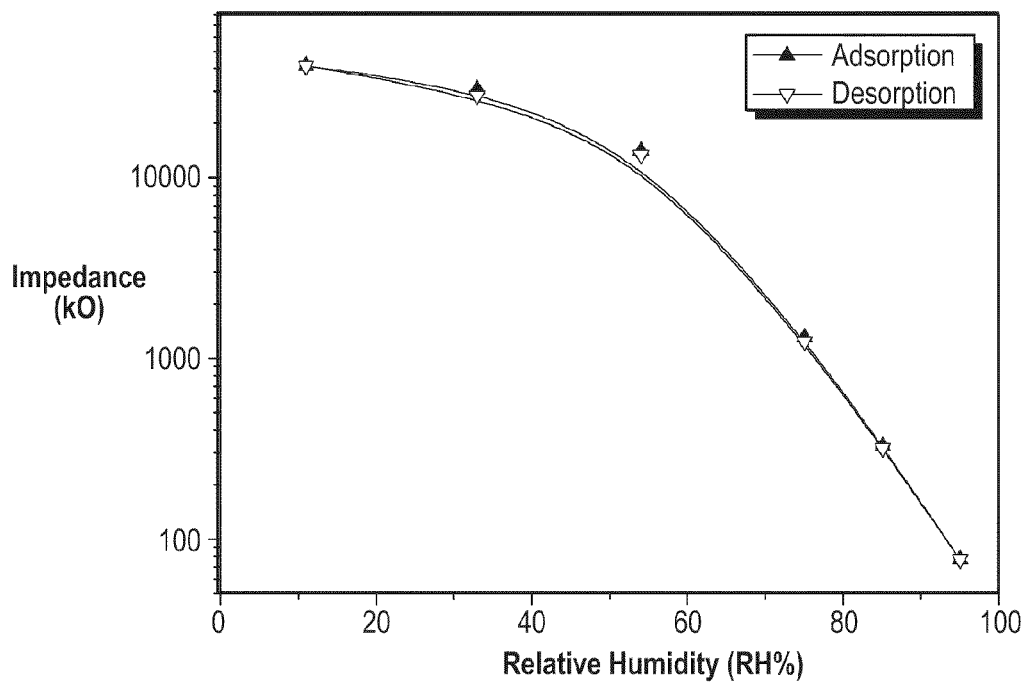
Figure 5E:
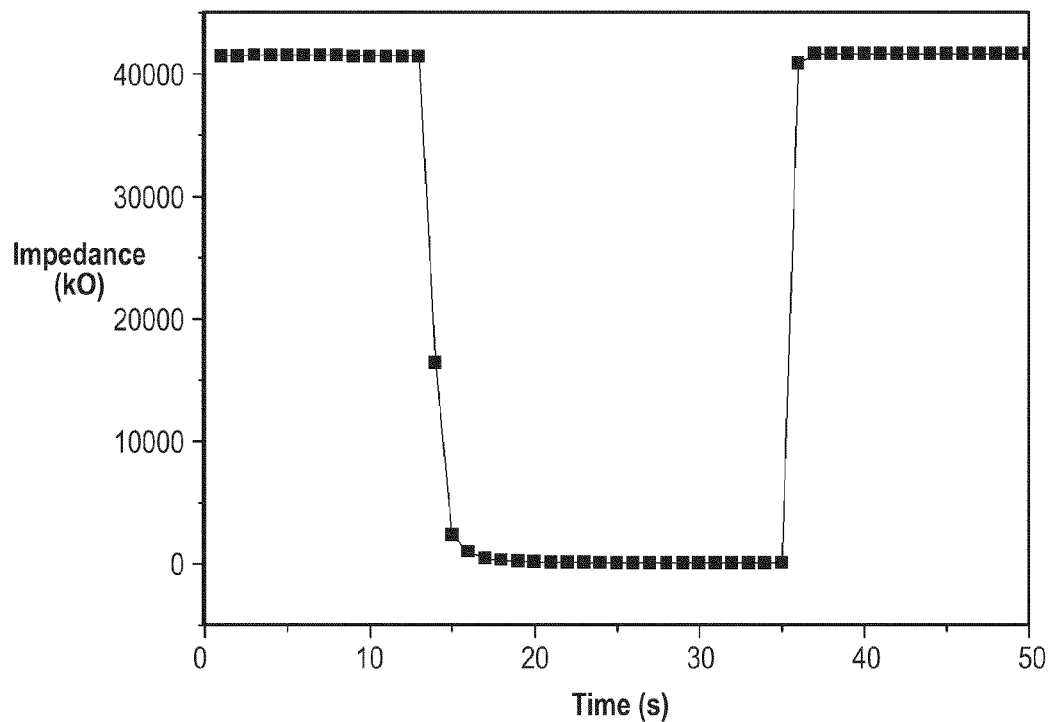
Figure 5F:
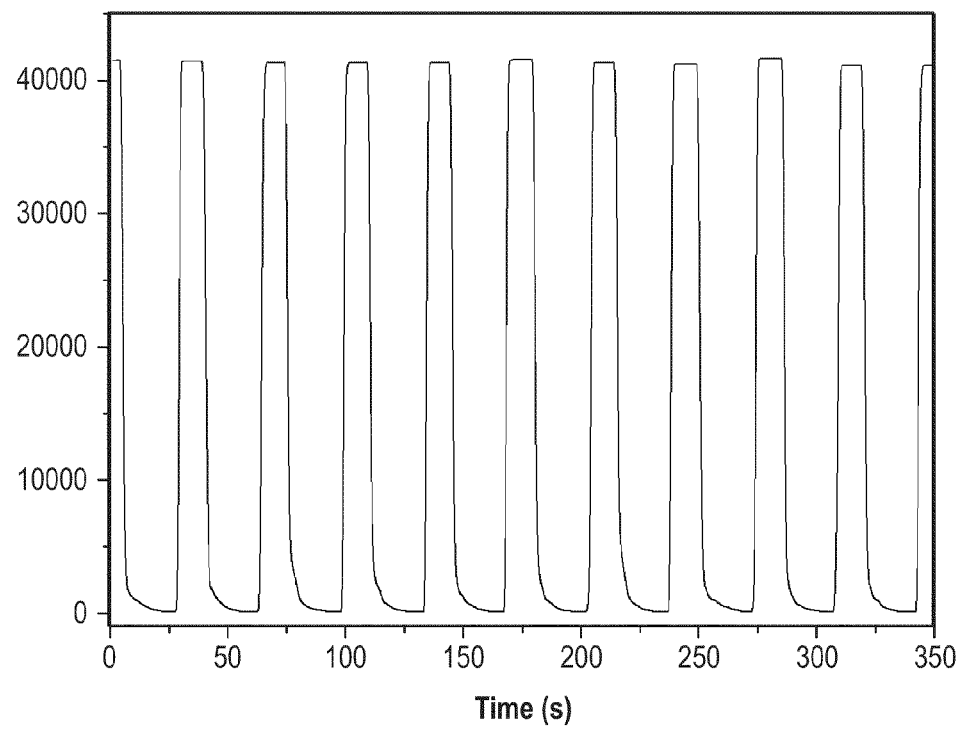

FIG. 5c reveals the response and recovery behaviors on the products as prepared at different temperatures. The humidity hysteresis characteristic of the as-prepared product at 600° C. is given in FIG. 5d, which confirms that there is no distinction between the absorption and desorption processes. FIGS. 5e and 5f show the response and recovery behaviors on the products prepared at 600° C., indicating that the response time is about 2 second and recovery time is about 1 second.

V. Stability of the As-Prepared Humidity Sensor

Figure 6:
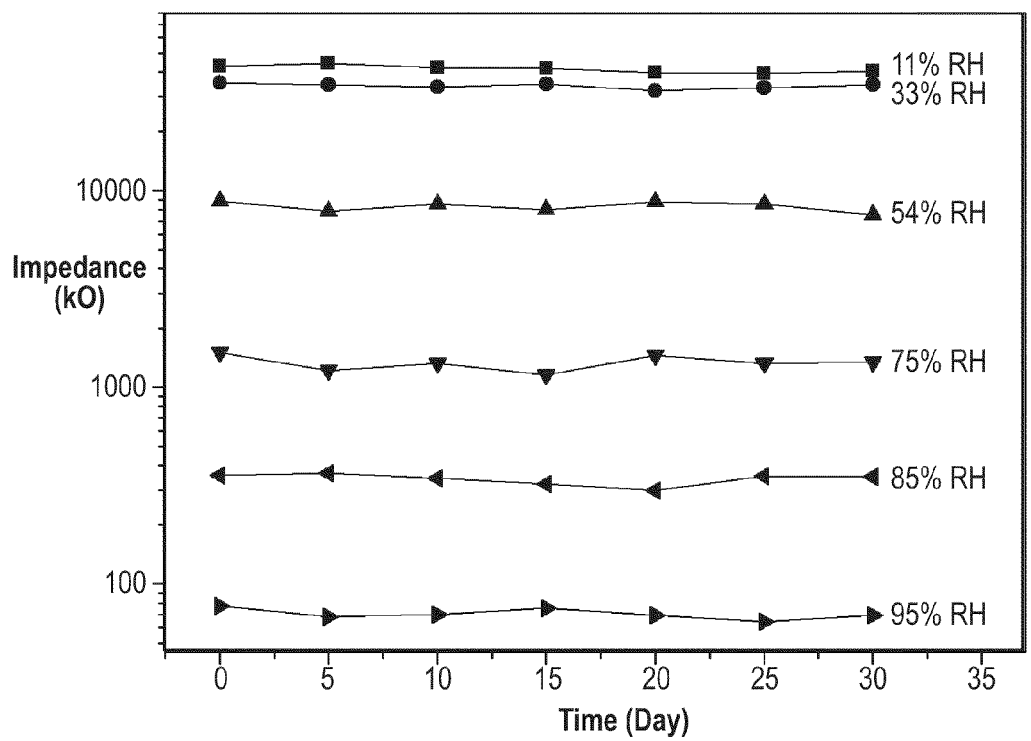
FIG. 6 is a graph depicting stabilities of the products for 30 days.

As the stability is an important characteristic for humidity sensors in practical applications, we put in air the working electrode covered with the product (600° C.) for one month and then characterize its impedances as shown in the graph of FIG. 6. Those impedances of the product hardly changed, confirming a good stability.

Additionally, as illustrated by Fujishima, *Adv. Mater.* 1998, 10, 135, $TiO_2$ is a photosensitive and self-cleaning material, and UV light can change the surface structures of $TiO_2$. When the $TiO_2$ structures are irradiated with UV light, the photogenerated hole reacts with lattice oxygen to form surface oxygen vacancies and the water molecules kinetically coordinate, and thus the humidity sensing properties based on $TiO_2$ structures will change.

Figure 7:
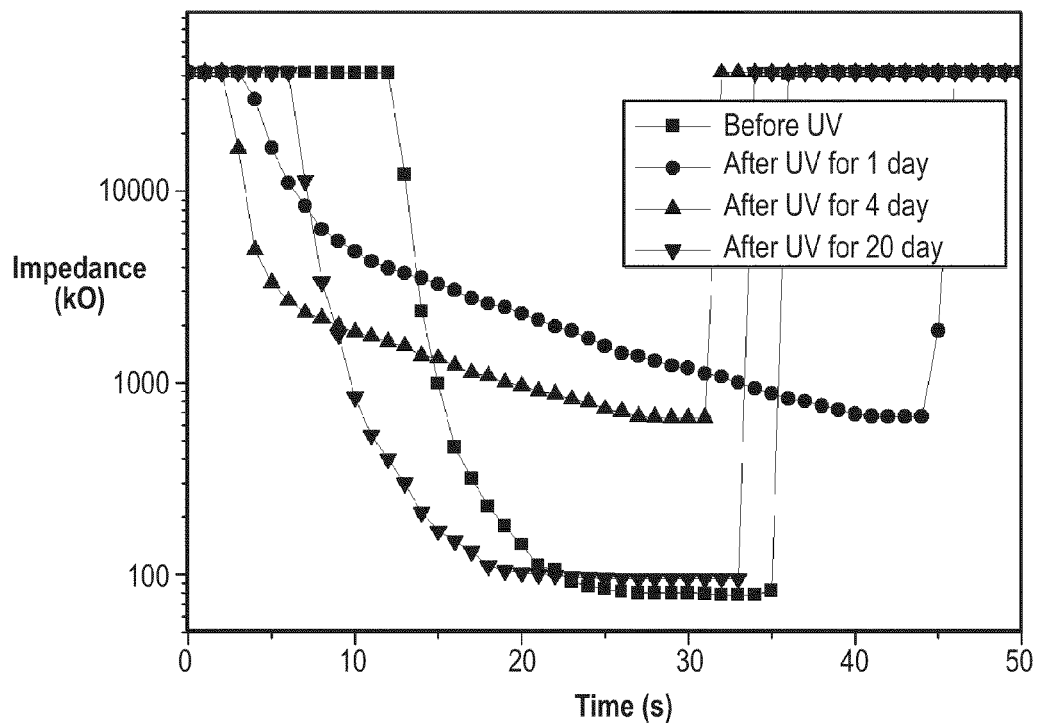
FIG. 7 is a graph depicting affection of UV irradiation on the humidity sensing characteristics based on inventive products.

FIG. 7 is a graph that shows the effects of UV light on the humidity sensing characteristics of our product (600° C.). After UV irradiation, those characteristics were weakened. When the product was put in darkness for 20 days, however, the characteristics resume or recover. Those results demonstrate good stability of the inventive product, even with regard to UV irradiation.

VI. Conclusions

In summary, we present a simple, effective, and low-cost route for $Mg^{2+}/Na^+$ doped $TiO_2$ nanofiber mats. The as-prepared products show good humidity sensing characteristics (super-rapid response time and recovery time, good reproducibility, and stability), which show promise in being applied in fabricating humidity nanosensors. As $TiO_2$ has been used as substrates, the inventive products can be also applied in photocatalysts, photovoltaics, sensors, and electrochromic display devices. More importantly, the disclosed method might not only open a new avenue for the synthesis of highly efficient humidity sensors, but also offer a platform to better understand and construct high effectively humidity nanodectors.

VII. Experimental

Materials: $MgCl_2$ (>95%), tetrabutyl titanate (>95%), ethanol (>95%) and acetic acid (>95%) were purchased from Tianjin Chemical Company. Poly (vinyl pyrrolidone) (Mw: 1,300,000) and dioctyl sulfosuccinate sodium (AOT: $C_{20}H_{37}OSNa$) were purchased from Aldrich.

Preparation of $Mg^{2+}/Na^+$ doped $TiO_2$ nanofibers: In a typical procedure, 1.5 g of tetrabutyl titanate was mixed with 3 mL of acetic and 3 mL of ethanol in a glovebox under vigorous stirring for 10 minutes. Subsequently, this solution was added to 7.5 mL of ethanol containing 0.45 g of poly (vinyl pyrrolidone) (PVP), 0.02 g of dioctyl sulfosuccinate sodium (AOT: $C_{20}H_{37}OSNa$), and a suitable amount of $MgCl_2$ under vigorous stirring for 30 min. Then, the mixture was loaded into a glass syringe and connected to high-voltage power supply. 12 kV was provided between the cathode (a flat foil) and anode (syringe) at a distance of 20 cm. Then, calcination (500° C. in air for 3 hours) has been used to treat the as-prepared nanocomposite fibers to remove PVP and convert tetrabutyl titanate into crystal $TiO_2$ nanofiber.

Fabrication and measurement of humidity sensor based on the disclosed product: The as-prepared $Mg^{2+}/Na^+$ doped $TiO_2$ nanofibers were mixed in a weight ratio of 100:5 and were ground with deionized water to form a dilute paste. The paste was screen-printed onto a ceramic substrate (6 mm×3 mm, 0.5 mm in thickness) with five pairs of Ag—Pd interdigital electrodes (electrodes width and distance: 0.15 mm) to form a film with the thickness about 10 μm, and then the film was dried at 60° C. in air for 5 hours. Finally, the humidity sensor was fabricated after aging at 95% relative humidity with a voltage of 1V, and frequency of 100 Hz for 24 hours.

The characteristic curves of humidity sensitivity were measured on a ZL5 intelligent LCR test meter (Made in Shanghai, China) at room temperature. The voltage applied in the studies was AC 1 V. The controlled humidity environments were achieved using supersaturation aqueous solutions of different salts of different salts of LiCl, $MgCl_2$, $Mg(NO_3)_2$, NaCl, KCl and $KNO_3$ in a closed glass vessel at room temperature, which yielded 11, 33, 54, 75, 85 and 95% RH, respectively.

Characterization: The X-ray powder diffraction (XRD) data were collected on an X'Pert MPD Philips diffractometer (Cu Kα X-radiation at 40 kV and 50 mA). Scanning electron microscopy (SEM) images was recorded on a SHIMADZU SSX-550 (Japan) instrument. The humidity measured machine was ZL5 intelligent LCR test meter made in Shanghai China.

A new type of highly efficient and self-cleaning humidity sensor based on $Mg^{2+}/Na^+$-doped $TiO_2$ nanofiber mats is provided. The examples show the response and recovery characteristic curves for ten circles with the RH changing from 11 to 95%.

Supporting Information

Figure 8:
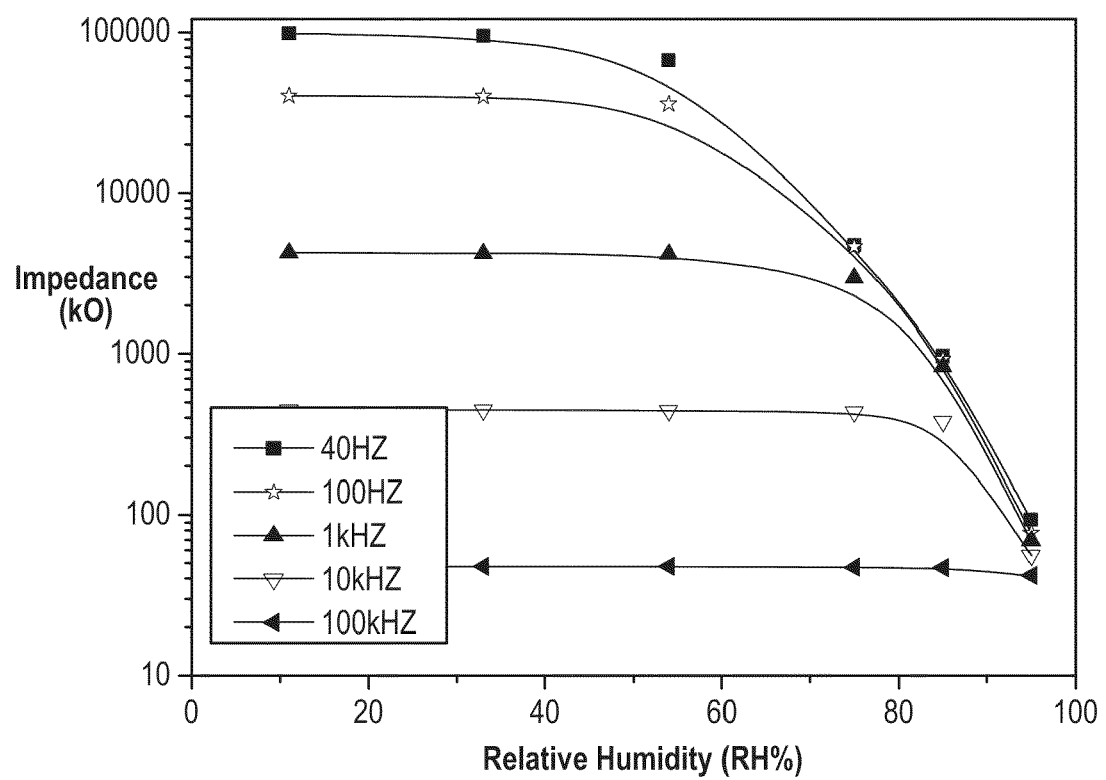
FIG. 8 is a graph depicting impedance dependence of relative humidity at various frequencies.

Explanation of FIG. 8: In order to find out the optimization relationship of sample between impedance and relative humidity, we measured the impedance at different frequencies. From the curve shown in FIG. 8, we found that the high humidity sensitivity and good linearity in whole relative humidity range are obtained in the low frequency region such as 40 and 100 Hz. The higher the frequency, the lower the sensitivity, which can be attributed to, that at higher frequencies, the adsorbed water cannot be polarized, therefore the dielectric phenomenon does not appear. At the same time, we found that when the frequency is 40 Hz, the measured data were unstable. In order to gain high relative humidity sensitivity over the entire relative humidity range and good linearity, low working frequency should be applied. So we confirm the operation condition at AC 1V, 100 Hz.

Figure 9A:
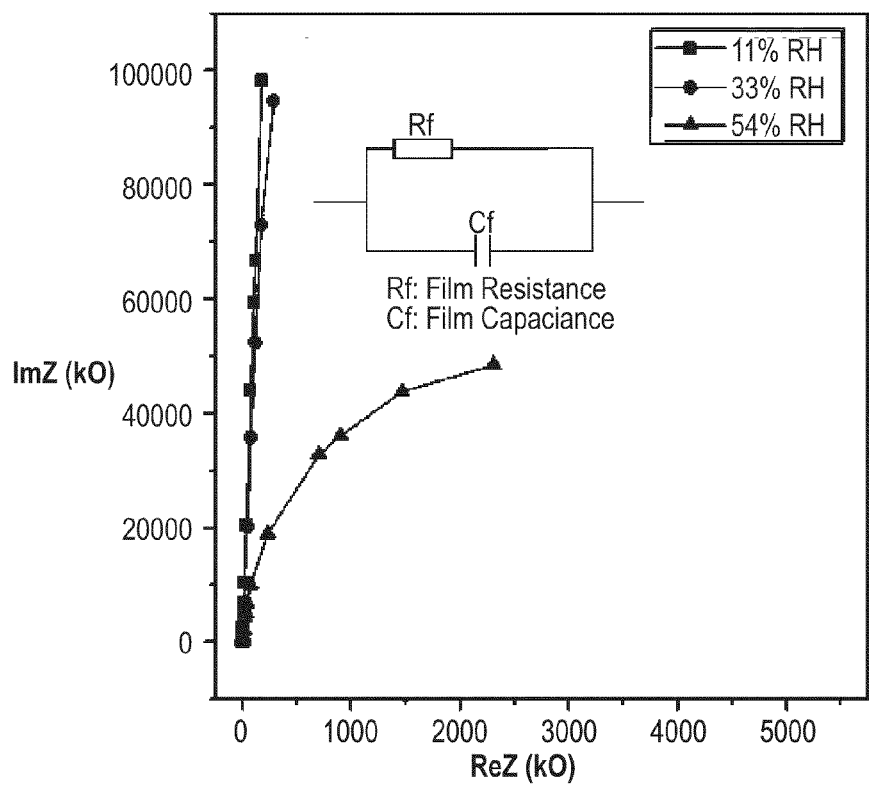
FIGS. 9a-b are graphs depicting as-prepared humidity sensor working principles.
Figure 9B:
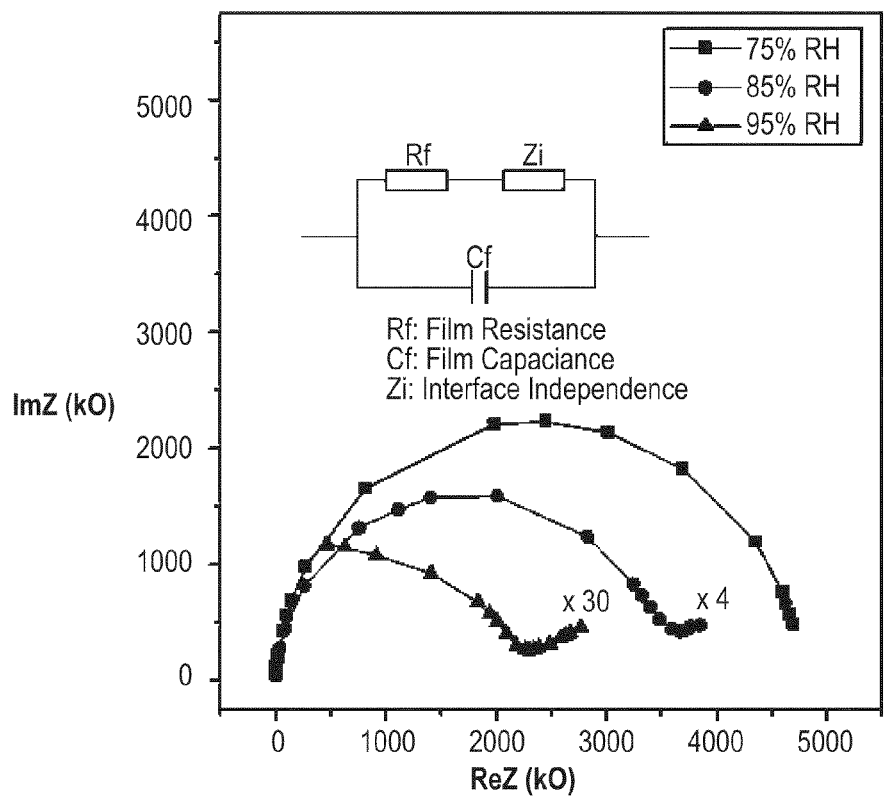
Figure 3A:
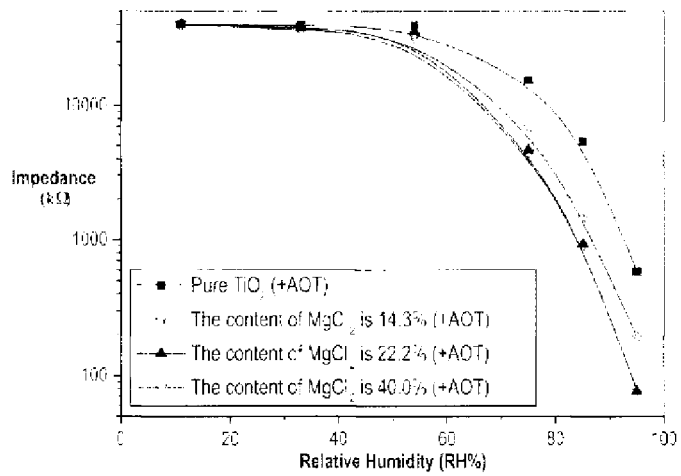
Figure 3B:
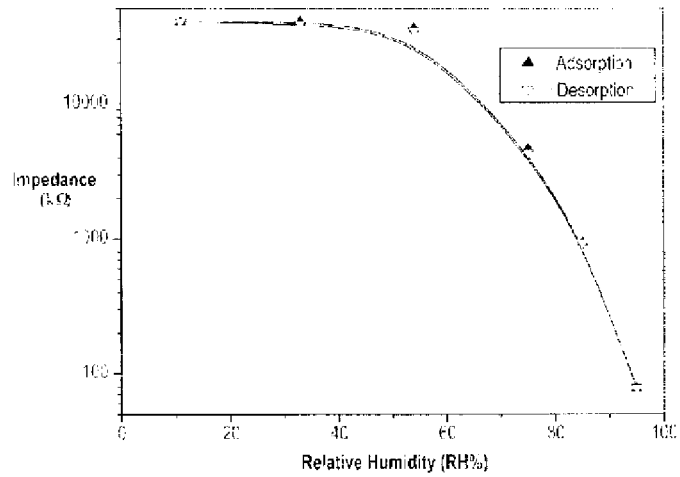
Figure 4A:
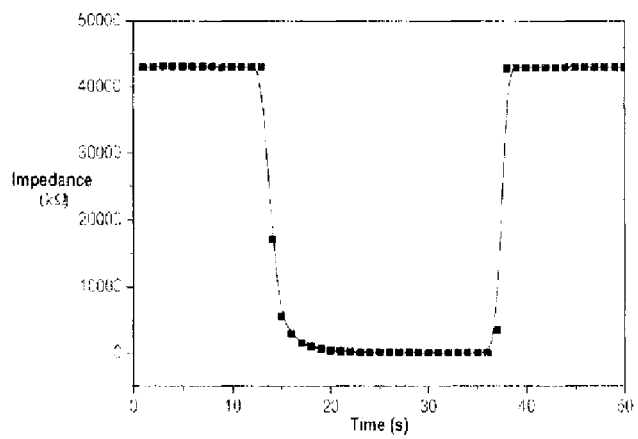
Figure 4B:
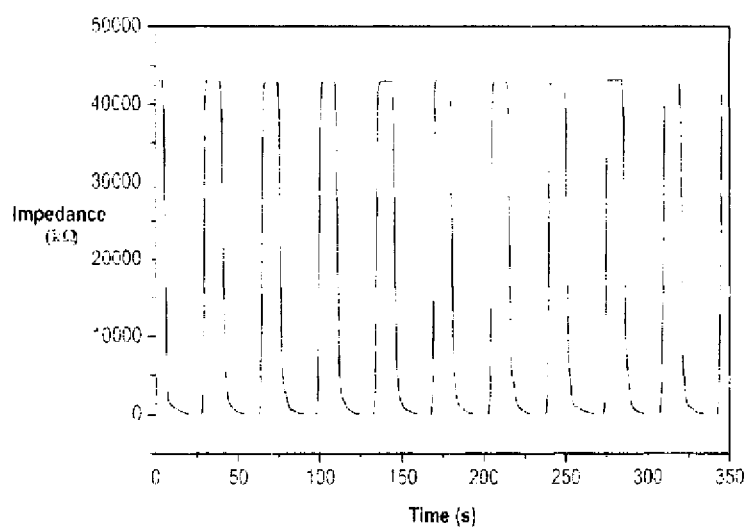
Figure 5A:
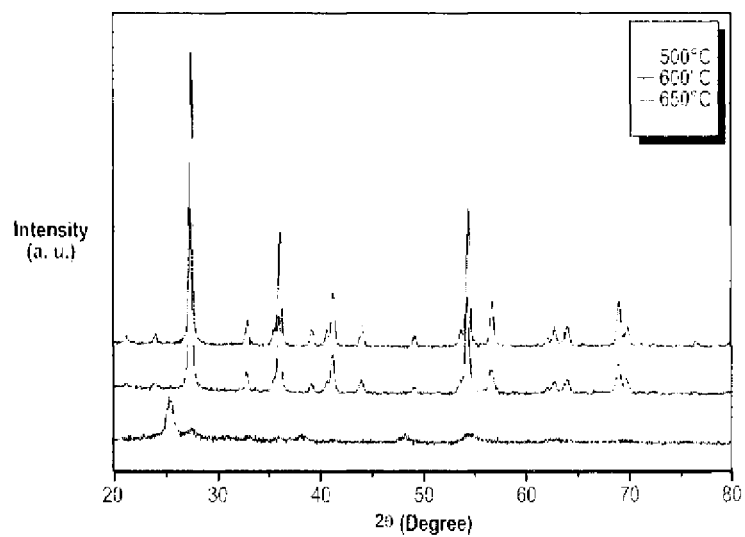
Figure 5B:
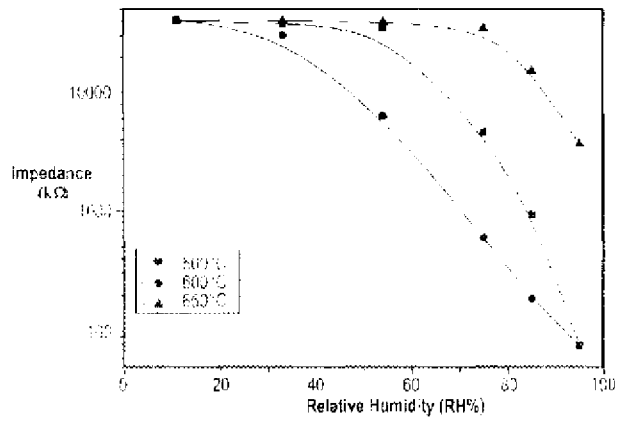
Figure 5C:
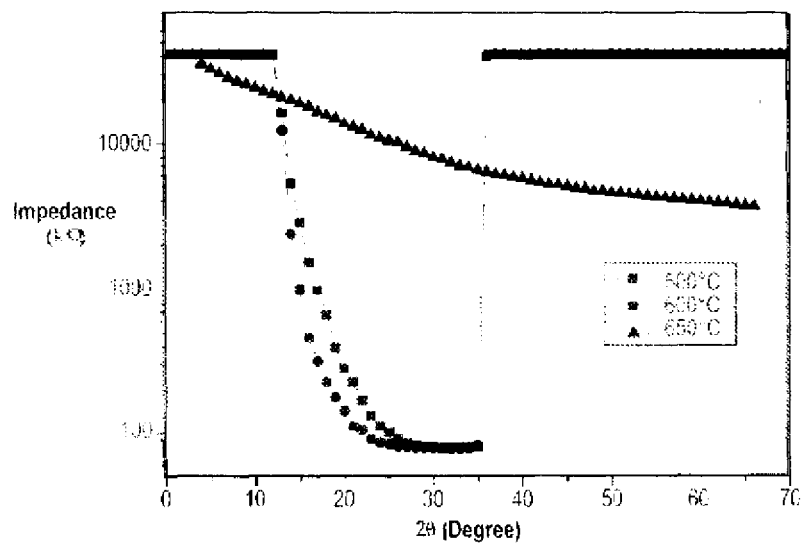
Figure 5D:
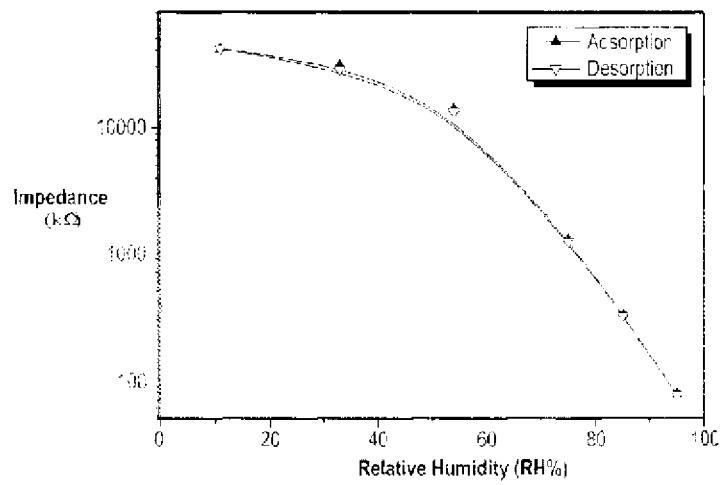
Figure 5E:
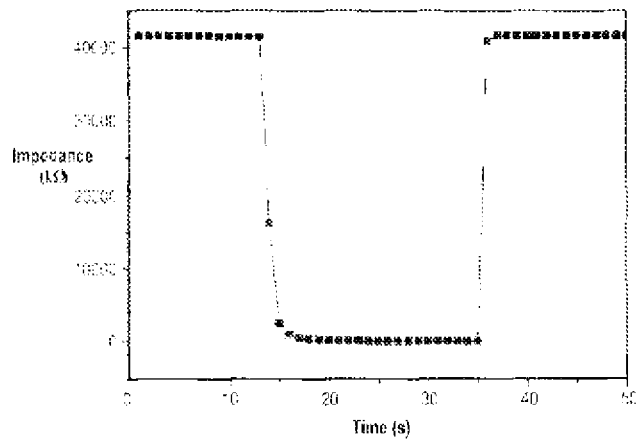
Figure 5F:
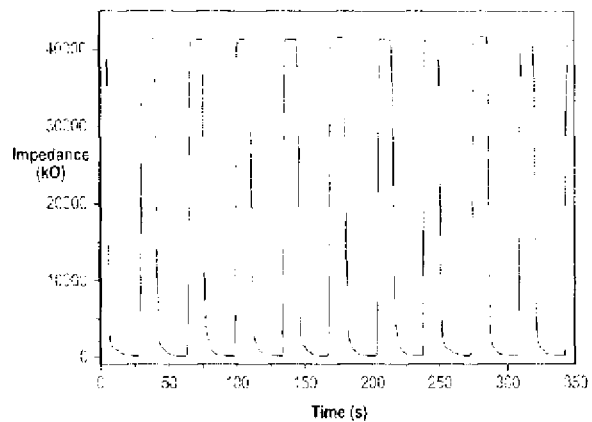
Figure 6:
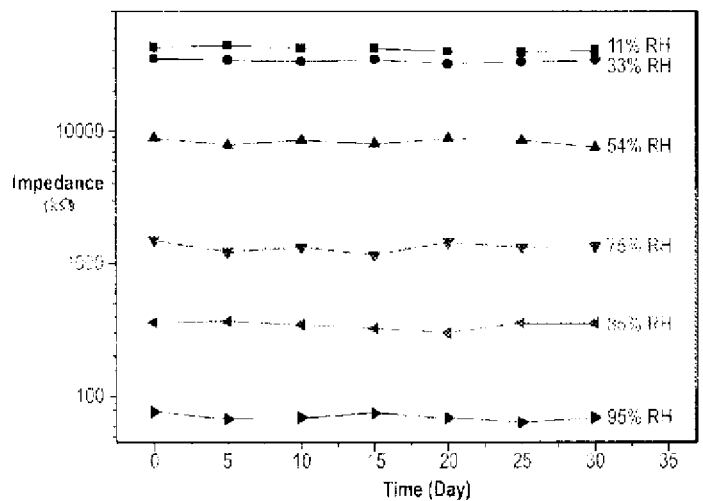
Figure 7:
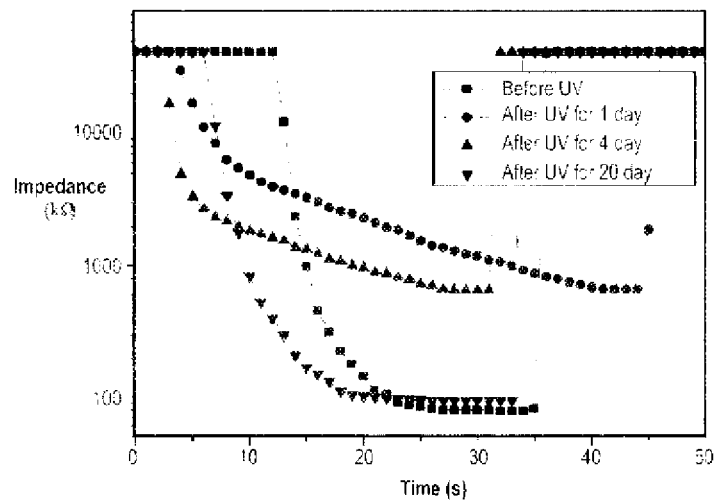
Figure 8:
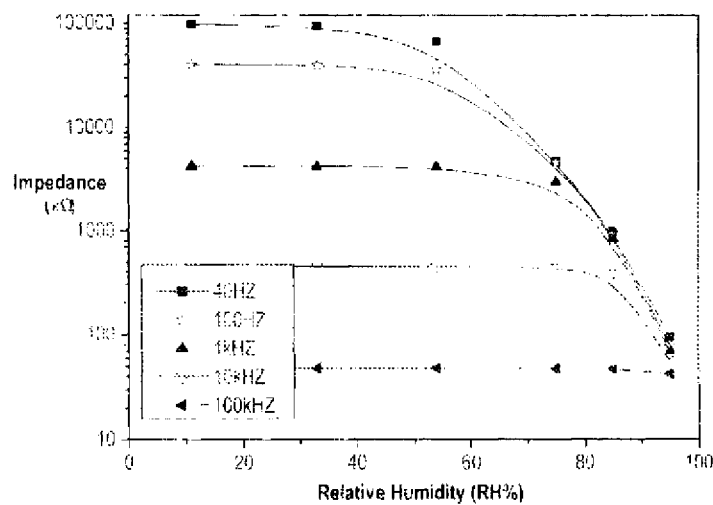
Figure 9A:
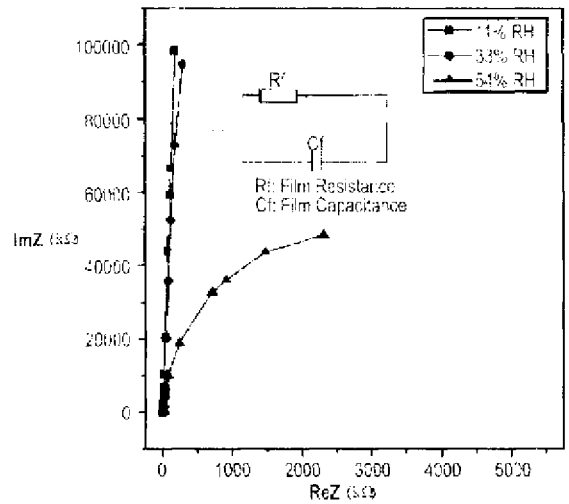

Explanation of FIGS. 9a-b: To understand our sensor working principles, the complex impedances have been measured. In our work, the frequency varies from 40 Hz to 100 Hz and the relative humidity ranges from 11% to 95% at room temperature. We measured the complex impedance and complex angle at different frequencies and different relative humidity, and then calculated the real part and the imaginary part of complex impedance. We can clearly see from the graphs in FIGS. 9a-b that at low relative humidity a half semicircle is observed in complex impedance plots. With increasing of relative humidity, the half semicircle increases and becomes a semicircle. Many authors have explained that the semicircle is due to a kind of polarization and can be modeled by an equivalent circuit of parallel resistor and capacitor. At this time, only a few water molecules are adsorbed. Since coverage of water on the surface is not continuous, the ionic conduction is difficult. Based on the mechanism of R. Schaub et al., *Phys. Rev. Lett.* 2001, 87, 226104, the tips and defects of the $TiO_2$ nanofibers present a high local charge density and a strong electrostatic field, which promotes water dissociation. The dissociation provides protons as charge carriers of the hopping transport (FIG. 9a).

When the relative humidity reaches a high value, a straight line appears after the semicircle in the low frequency, which was caused by the diffusion process of redox ions at the electrode/sensing film interface (FIG. 9b). In this condition, one or several serial water layers are formed among $TiO_2$ nanofibers, and ionic conduction between nanorods takes place along with protonic transport, and becomes dominating in the transport-process. The equivalent circuits of such complex impedance plots have been inserted in FIGS. 9a-b. Here $R_f$ represents the resistance of the KCl doped $TiO_2$ nanofibers film, which decreases as relative humidity increases. $C_f$ represents the capacitance of the film and $Z_i$ the impedance at the electrode/sensing film interface.

According to FIG. 9a, $R_f \ll Z_i$ at low relative humidity, and the impedance change of the sensor is mostly determined by $R_f$. At high relative humidity (FIG. 9b), the magnitude of $R_f$ and $Z_i$ are the same and the impedance change of the sensor is determined by both $R_f$ and $Z_i$. So from the view of the complex impedance plots, the sensing principle of this material is proton and ionic conductivity in low and high relative humidity, respectively.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope

What is claimed is:

1. A method for making a nanofiber for use in a humidity sensor, comprising:
   providing a titanium compound;
   mixing the titanium compound with a magnesium compound, a sodium compound, and a high molecular weight polymer material to form a mixture;
   electrospinning the mixture to form composite nanofibers; and
   calcining the composite nanofibers to yield a $TiO_2$ nanofiber material doped with magnesium and sodium.

2. A method as in claim 1, wherein the doped $TiO_2$ nanofiber material forms a nanofiber mat.

3. A method as in claim 1, wherein the high molecular weight polymer material comprises at least one of polyvinyl alcohol or polyvinyl pyrrolidone.

4. A method as in claim 1, wherein the high molecular weight polymer material has a molecular weight of about 300,000 or greater.

5. A method as in claim 1, wherein the high molecular weight polymer material has a molecular weight of about 1,000,000 or greater.

6. A method as in claim 1, further comprising sonicating the $TiO_2$ nanofiber material.

7. A method as in claim 1 in which the composite nanofibers are calcined at a temperature of about 500° C. or greater.

8. A method as in claim 1 in which the composite nanofibers are calcined at a temperature of about 600° C. or greater.

9. A method as in claim 1 in which the composite nanofibers are calcined at a temperature in a range from about 500° C. to about 650° C.

10. A method for making a humidity nanosensor comprising depositing the $TiO_2$ nanofiber material manufactured according to the method of claim 1 onto an electrode configured to sense humidity in combination with the $TiO_2$ nanofiber material.

11. A method of detecting the relative humidity of a gaseous mixture comprising exposing a humidity sensor manufactured according to the method of claim 10 to a gaseous mixture that includes water vapor and detecting a change in an electrical output of the humidity nanosensor.

12. A method for making a humidity nanosensor as in claim 10, wherein the $TiO_2$ nanofiber material is formed as a mat on the electrode.

13. A method for making a humidity nanosensor as in claim 12, wherein the electrode is an interdigital electrode.

14. A method for making a humidity nanosensor as in claim 10, wherein the electrode includes a noble metal.

15. A method as in claim 1, wherein the $TiO_2$ nanofiber material includes nanofibers having a width in a range about 10 nm to about 600 nm.

16. A method as in claim 1, wherein the $TiO_2$ nanofiber material includes nanofibers having a width in a range about 50 nm to about 300 nm.

17. A method as in claim 1, wherein the titanium compound is a tetravalent organometallic compound of titanium, the magnesium compound is an inorganic salt of magnesium, and the sodium compound is an organometallic sodium compound.

18. A method as in claim 1, wherein the tetravalent organometallic compound of titanium comprises tetrabutyl titanate, the inorganic salt of magnesium comprises magnesium chloride, and the organometallic sodium compound comprises dioctyl sulfosuccinate sodium.

19. A method for making a nanofiber for use in a humidity sensor, comprising:
   providing tetrabutyl titanate;
   mixing the tetrabutyl titanate with a magnesium compound, a sodium compound, and a high molecular weight polymer material to form a mixture;
   electro spinning the mixture to form composite nanofibers; and
   calcining the composite nanofibers to yield a $TiO_2$ nanofiber material doped with magnesium and sodium.

20. A method for making a nanofiber for use in a humidity sensor, comprising:
   providing a tetravalent organometallic compound of titanium;
   mixing the tetravalent organometallic compound of titanium with an inorganic salt of magnesium, an organometallic sodium compound, and a high molecular weight polymer material to form a mixture;
   electro spinning the mixture to form composite nanofibers; and
   calcining the composite nanofibers to yield a $TiO_2$ nanofiber material doped with magnesium and sodium.

* * * * *

UNITED STATES PATENT AND TRADEMARK OFFICE
CERTIFICATE OF CORRECTION

PATENT NO. : 8,225,641 B2
APPLICATION NO. : 12/544989
DATED : July 24, 2012
INVENTOR(S) : Wang et al.

Page 1 of 10

It is certified that error appears in the above-identified patent and that said Letters Patent is hereby corrected as shown below:

Drawings
Sheet 2, replace Figure 2D with the figure depicted below, wherein "2θ" replaces "20"

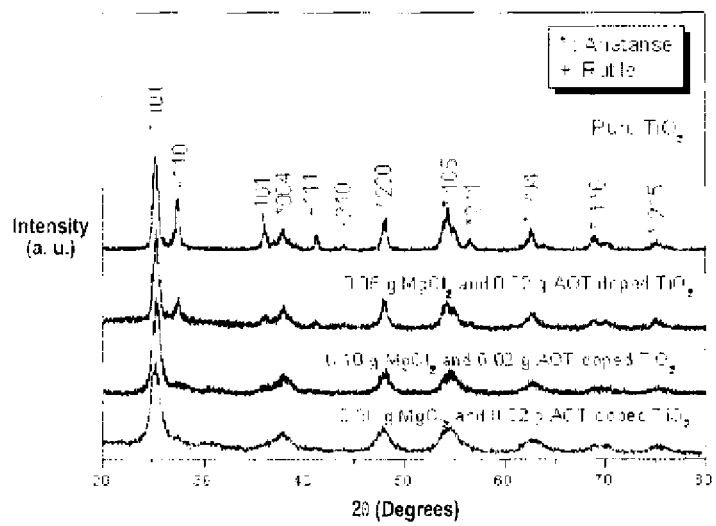

FIG. 2D

Signed and Sealed this
Seventh Day of May, 2013

Teresa Stanek Rea
*Acting Director of the United States Patent and Trademark Office*

Sheet 3, replace Figure 3A with the figure depicted below, wherein "kΩ" replaces "kO"

Sheet 3, replace Figure 3B with the figure depicted below, wherein "kΩ" replaces "kO"

Sheet 4, replace Figure 4A with the figure depicted below, wherein "kΩ" replaces "kO"

Sheet 4, replace Figure 4B with the figure depicted below, wherein "kΩ" replaces "kO"

Sheet 5, replace Figure 5A with the figure depicted below, wherein "2θ" replaces "20"

Sheet 5, replace Figure 5B with the figure depicted below, wherein "kΩ" replaces "kO"

Sheet 6, replaced Figure 5C with the figure depicted below, wherein "kΩ" replaces "kO" and "2θ"

replaces "20"

Sheet 6, replace Figure 5D with the figure depicted below, wherein "kΩ" replaces "kO"

Sheet 7, replace Figure 5E with the figure depicted below, wherein "kΩ" replaces "kO"

Sheet 7, replace Figure 5F with the figure depicted below, wherein the y-axis label "Impedance (kΩ)" has been added Sheet 8, replace Figure 6 with the figure depicted below, wherein "kΩ" replaces "kO"

Sheet 8, replace Figure 7 with the figure depicted below, wherein "kΩ" replaces "kO"

Sheet 9, replace Figure 8 with the figure depicted below, wherein "kΩ" replaces "kO"

Sheet 10, replace Figure 9A with the figure depicted below, wherein "capacitance" replaced the word "capaciance", "ImZ (kΩ)" replaced "ImZ (kO)", and "ReZ (kΩ)" replaced "ReZ (kO)"

Sheet 10, replace Figure 9B with the figure depicted below, wherein the word "capacitance'" replaced

CERTIFICATE OF CORRECTION (continued)
U.S. Pat. No. 8,225,641 B2 the previous word "capaciance", "ImZ (kΩ)" replaced "ImZ (kO)", and "ReZ (kΩ)" replaced "ReZ (kO)"

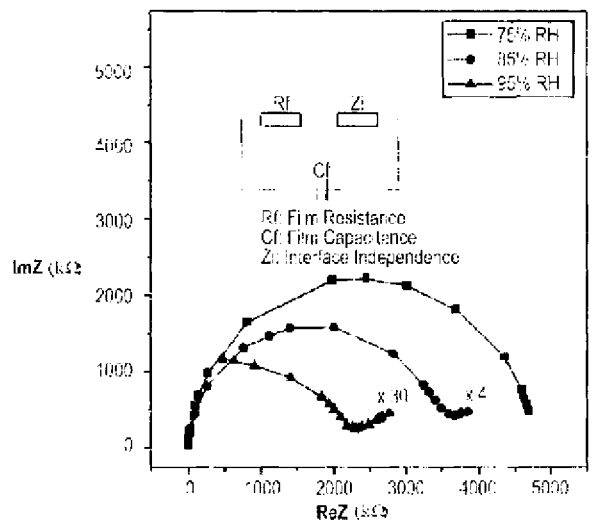

FIG. 9B

In the Specifications

Column 1
Line 36, change "high" to --highly--
Line 62, change "1,000,000." to --1,000,000).--

Figure 2D:
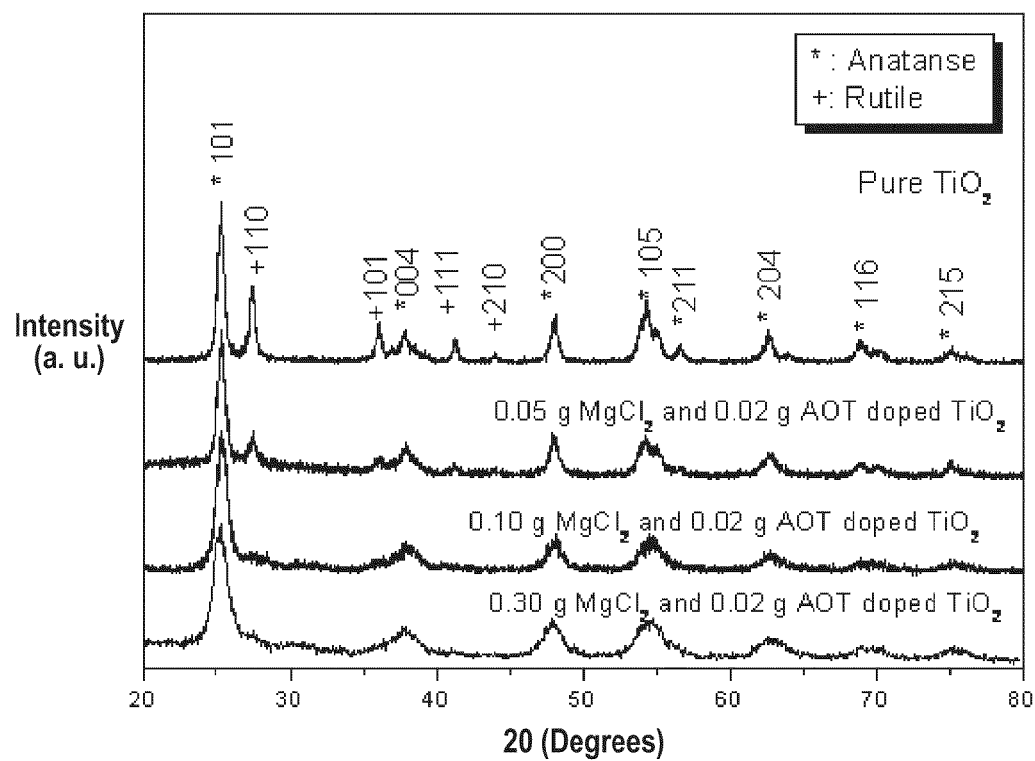

Column 3
Line 19, change "FIG. 1*d*" to --FIG. 2*d*--

Column 4
Line 21, change "has" to --have--
Line 28, change "making" to --leaving--
Line 45, change "Those impedances" to --The impedances--
Line 46, change "a good stability." to --good stability.--
Line 59, change "Those results" to --The results--

Column 5
Line 9, change "high effectively" to --highly effective--
Line 29, change "has been" to --was--
Line 48, change "salts of different salts of" to --salts of--
Line 55, change "measured" to --measuring--

Column 6

Line 6, change "to, that at" to --to the fact that--
Line 6-7, change "frequencies," to --frequencies--
Line 12, change "confirm" to --confirmed--
Line 44, change "dominating" to --dominant--

Column 8
Line 6, change "in a range" to --in a range of--
Line 9, change "in a range" to --in a range of--
Line 27, change "electro spinning" to --electrospinning--
Line 39, change "electro spinning" to --electrospinning--